United States Patent [19]

Franetzki et al.

[11] 4,270,532
[45] Jun. 2, 1981

[54] DEVICE FOR THE PRE-PROGRAMMABLE INFUSION OF LIQUIDS

[75] Inventors: Manfred Franetzki, Uttenreuth; Klaus Gagneur, Bubenreuth; Karl Prestele, Erlangen, all of Fed. Rep. of Germany

[73] Assignee: Siemens Aktiengesellschaft, Berlin & Munich, Fed. Rep. of Germany

[21] Appl. No.: 969,200

[22] Filed: Dec. 13, 1978

[30] Foreign Application Priority Data

Dec. 28, 1977 [DE] Fed. Rep. of Germany ....... 2758368

[51] Int. Cl.³ .............................................. A61M 5/20
[52] U.S. Cl. .................................................. 128/213 R
[58] Field of Search ............... 128/213, 214 E, 214 F, 128/260

[56] References Cited

U.S. PATENT DOCUMENTS

| | | | |
|---|---|---|---|
| 2,979,055 | 4/1961 | De Beer et al. | 128/214 E |
| 3,163,176 | 12/1964 | Darling | 128/214 E |
| 3,543,752 | 12/1970 | Hesse et al. | 128/214 E |
| 3,790,042 | 2/1974 | McCormick et al. | 128/214 E |
| 3,809,871 | 5/1974 | Howard et al. | 128/214 E |
| 4,077,405 | 3/1978 | Haerten et al. | 128/214 F |
| 4,114,144 | 9/1978 | Hyman | 128/214 E |
| 4,126,029 | 3/1979 | Ellinwood, Jr. | 128/260 |

FOREIGN PATENT DOCUMENTS

2451424 5/1976 Fed. Rep. of Germany.

Primary Examiner—William E. Kamm
Attorney, Agent, or Firm—Hill, Van Santen, Steadman, Chiara & Simpson

[57] ABSTRACT

Particularly for diabetes therapy, it is desirable to continuously infuse insulin in varying installments into the body of the patient. A control device serves as a program transmitter for a microdosing unit. The physician should be able to pre-program the daily profile of the infusion and, if necessary, to change it. According to the disclosure, at least the control device for the microdosing unit has memory means for a prescribable control program allocated to it, whereby the control program is pre-programmable in discrete time steps by an external programming device corresponding with a 24 hour daily sequence. The control device is detachably connected directly with the programming device or is coupled therewith by means of a program carrier or a programmed memory chip solely for a rapid transfer of the pre-programmed control program into the internal memory means of the control device. Thus the control device is particularly adapted for the adjustment of diabetes patients to an optimum daily profile of insulin administration outside of a hospital setting.

1 Claim, 4 Drawing Figures

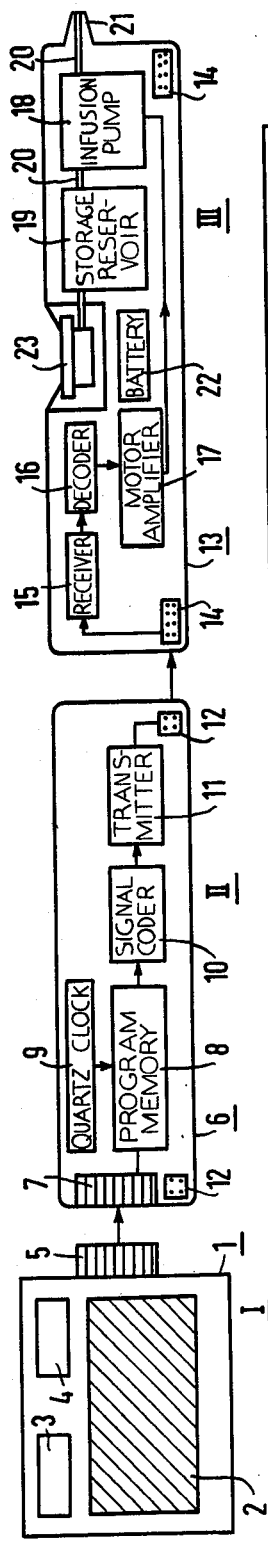
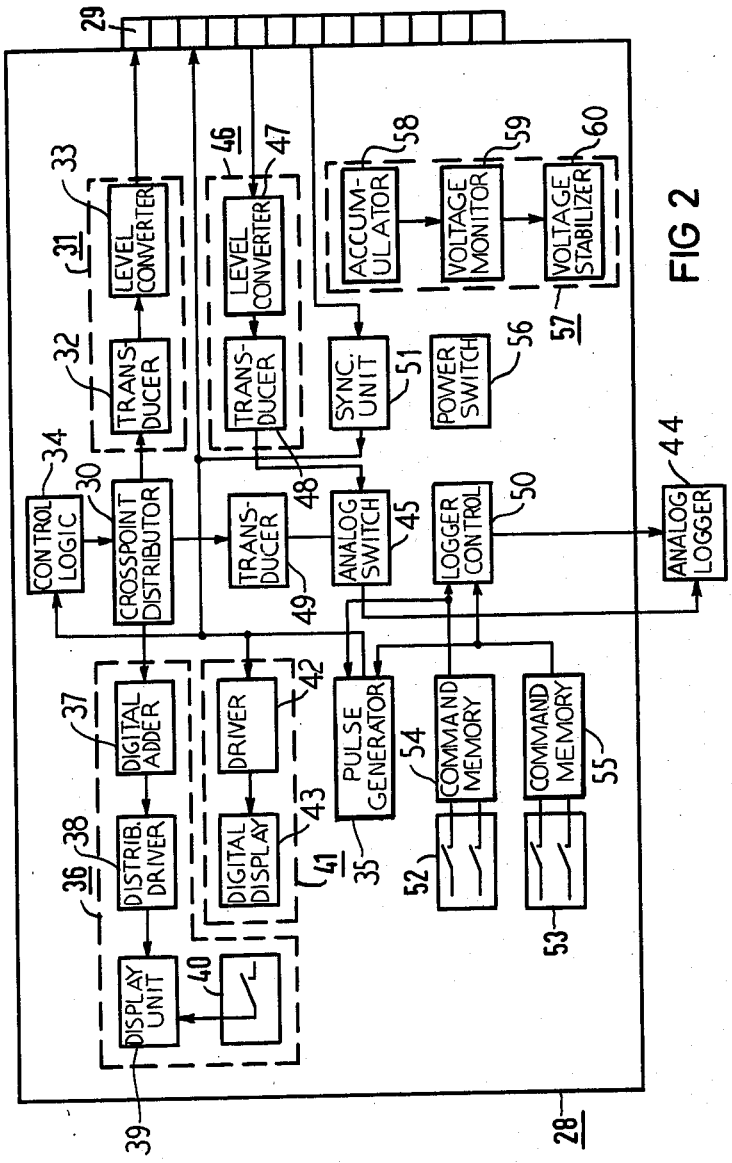

DEVICE FOR THE PRE-PROGRAMMABLE INFUSION OF LIQUIDS

BACKGROUND OF THE INVENTION

The invention relates to a device for the pre-programmable infusion of liquids into the human or animal body, particularly for the administration of insulin in diabetes therapy, consisting of a microdosing unit for the liquid as well as a control device as a program transmitter for the microdosing unit. Thereby, the microdosing unit for the liquid can be implanted in the body together with or separate from the control device or can be carried externally on the body surface.

In diabetes therapy, it is desirable to continuously infuse insulin into the body of the patient at varying installments, because the need of the diabetic for insulin during the day is subject to great fluctuations, determined, for example, by the rhythm of the meals. It has been shown that—as long as no infusion devices that regulate themselves automatically by means of glucose sensors are available—the delivery of insulin should best ensue according to a daily profile that can be individually adjusted and pre-programmed for the patient. An apparatus for the supply of liquids to the human or animal body is known in which an electric program transmitter is present, which can be pre-programmed to a program extending over prescribed time steps by an operator with manually adjustable control signals of varying magnitudes. Thereby, the control signals are adjusted in a practical manner by means of a crosspoint distributor. Although such an apparatus is specifically conceived as a "bedside apparatus", nonetheless the advantages of such an apparatus control can also be transferred in principle to a microdosing unit which can be carried on the body or implanted in the body, respectively.

However, in a device with a microdosing unit which is carried on or in the body of the patient, it must be guaranteed that the pre-programming of the infusion device to the desired daily profile can be carried out by the physician in a simple and clear manner. In the treatment of diabetics, for example, cases occur in which an optimum daily infusion profile for an infusion unit to be implanted subsequently or also for a traditional injection therapy to be carried out later is to be ascertained during a longer examination period, during which the patient is located in the hospital under the supervision of the physician. Thereby, the patient should be able to move about freely all day and all night during the administration of the insulin. For such applications, the devices known from prior art are not optimally suited.

SUMMARY OF THE INVENTION

The object of the invention, therefore, is to eliminate this deficiency. A further, improved device for the infusion of liquids into the human or animal body is to be designed which can be comfortably carried and which also does not disturb during sleep. Such a device should be pre-programmable with a plurality of discrete infusion installments in sufficiently small time slot patterns for 24 hours. Thereby, the physician should be given the possibility to change the control program of the infusion at any time. The total amount of the pre-programmed, daily administration of medicine should be directly accessible and should also be printable as an analog curve for the optical monitoring of the daily profile. Thereby, malfunctioning of the device should be rendered essentially impossible by means of monitoring and alarm signal indications.

The object is inventively achieved in that at least the control installation for the microdosing unit has memory means allocated to it for a prescribable control program, whereby the control program is pre-programmable in discrete time steps corresponding to the 24-hour daily sequence at an external programming device; and in that the control installation is electrically connected with the programming device or with the program carrier solely for rapid transfer of the pre-programmed control program into the internal memory means.

The infusion device now created consists essentially of individual devices separated in two functional groups: the microdosing unit, the corresponding control unit and the external programming device. By means of the separation into these functional units, the application of the infusion device becomes more varied. The microdosing unit with its corresponding control unit is carried by the patient on his body, whereas the programming device is stationary and is at the disposal of the physician for other tasks. Thereby, the microdosing unit, for example, is arranged directly and securely on the body of the patient for infusion, whereas the control device is carried in a pocket, or something similar, for easy access. Optionally, the microdosing unit can be implanted in the body of the patient. A daily profile corresponding to the individual needs of a patient is programmed-in by the physician at the stationary programming device as needed, which daily profile then is rapidly transferred into internal memory means of the control installation as a fixed program by means of a brief connection of the programming device and the control device and assumes the control of the microdosing unit for longer time spans.

The programming device is preferably designed as an electric distributor, for example, as a crosspoint distributor, with manually adjustable control points. As an alternative, this distributor can be designed as an infusion installment switch, with which the physician can adjust discrete infusion installments temporally pulsed-through in correspondence with a chronologically succeeding sequence. In an advantageous further development, a daily profile of the dosing is impressed on separate program carriers by means of the programming device, which program carriers can be read by the control installation by means of a reading unit for rapid transfer into the internal memory. Punched cards, punched tapes or magnetic cards, for example, may be used as program carriers.

Such a further development has the advantage that, upon a suitable coding, a daily profile of the infusion can be represented punched on punched cards or punched tapes practically as an analog curve which can be immediately recognized and classified visually by the user, whereby such punched cards or punched tapes can be stored in archives in a simple manner. In that manner, corresponding program libraries can be built up, from which the access to an individual program can ensue quickly. If the daily profile of the dosing is coded onto magnetic cards or something similar, then it is meaningful to rapidly read out the analog curve of the dosing to a logger than can be connected to the programming device for checking.

In these cases, the control installation exhibits a program reader in addition to the memory. The read in of the control program then ensues in such manner that a punched card, punched tape or magnetic card is input into the control device and the stored program thereon is transferred into the internal memory of the control device. It is also possible to design the memory of the control device interchangeably, so that this memory can be directly pre-programmed on the external programming device. A separate reading installation in the control device is then superfluous; the transfer of the program is then reduced to an exchange of the memory.

In the following, further details of the invention are explained in the descriptions of sample embodiments on the basis of the accompanying sheets of drawings; and other objects, features and advantages will be apparent from this detailed disclosure and from the appended claims.

BRIEF DESCRIPTION OF THE DRAWINGS

FIG. 1 shows a basic circuit diagram of a device according to the invention;

FIG. 2 shows a block diagram of a specific programming device with crosspoint distributor;

DETAILED DESCRIPTION

Figure 3:
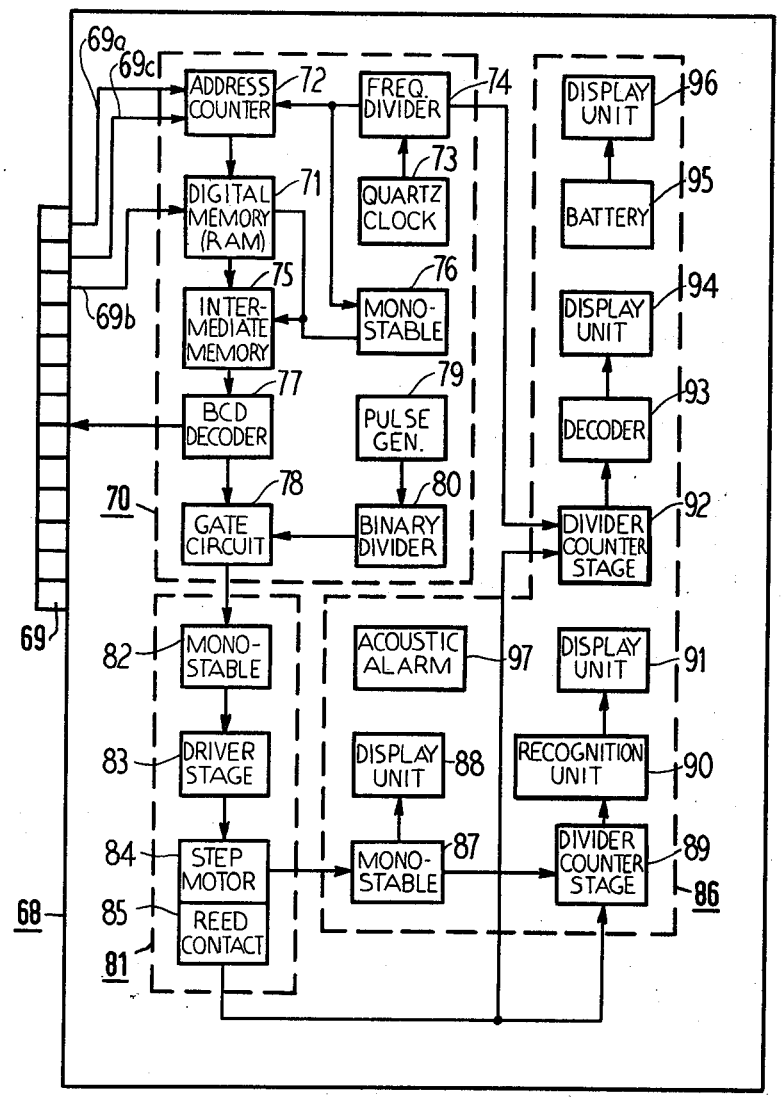
FIG. 3 is a block diagram of a specific control device into which, in addition, pump drive control and monitoring of the microdosing unit are integrated.

In FIG. 1, an external programming device is indicated at I, a control installation at II, and the microdosing unit at III. The individual devices I and II are briefly connected mechanically and electrically solely for the purpose of transferring the program, whereas the individual devices II and III are connected for the continuing signal transmission upon the functioning of the microdosing unit. Thereby, the signal transmission ensues via a direct line or wirelessly by means of remote control. In particular, in the sample embodiment according to FIG. 1, an inductive signal transmission is applied. The device I contains a housing 1 with an electrical distributor, in particular, a crosspoint distributor. The reference numeral 2 characterizes the programming array of the signal distributor. Further, visual and control display units 3 and 4 and a programming plug 5 are arranged on the housing 1. The device II consists of the housing 6, which exhibits an external plug socket 7 which fits with the plug 5. The housing 6 comprises, as its essential component part, a memory 8 for storing the daily program pre-programmed by means of the programming device I. The program memory 8 has a quartz clock 9 allocated to it as a timer, as well as a signal coder 10 with a transmitter 11 connected on its output side and a transmission coil 12 connected on its output side, by means of which the signal polled from the program memory is prepared for transmission. The transmission coil 12 extends about the entire perimeter of the base of the housing 6 and is indicated at the opposite corners as a section.

The housing of the microdosing unit III is indicated at 13. Analogous to the control installation II, it contains a corresponding reception coil 14 extending about the perimeter of its base with an electronic receiver 15 and decoder 16 connected on the outlet side. A motor amplifier 17 is controlled via the decoder 16, with which motor amplifier the drive motor of a mechanical pump 18 is driven. By means of the pump 18, the liquid insulin is conveyed out of a storage reservoir 19 to a catheter connection 21 on the device housing 13 via a connection line 20 and is delivered into the body of the patient. Further, the housing 13 of the microdosing unit I also contains a battery 22 as an energy source for the pump drive as well as a refilling valve 23, via which insulin can be refilled into the storage reservoir by means of an injection through a membrane that automatically closes itself-transcutaneously in the case of an implanted microdosing unit, if necessary.

In FIG. 2, the programming device (corresponding to device I of FIG. 1) is shown with a housing 28 and a program plug 29 and comprises the electrical or, respectively, electronic component parts 30 through 60 in the circuit described as follows: a read path 31, which consists of a rate-binary transducer 32 and a level coverter 33 connected on its output side, is allocated to an electric crosspoint distributor 30. Via a control logic 34, which is driven by a pulse generator 35 for the generation of working and shift pulses, the electrical signal value that was manually adjusted on the crosspoint distributor 30 is tapped by means of shift registers and transduced into a binary signal by means of transducer 32. By means of level converter 33, the binary signal is matched to the required signal level, which can then be directly registered by the control device II. The electric signal values manually adjusted on the crosspoint distributor 30 are further delivered to a unit 36 for dosage display. This unit 36 consists, in detail, of a digital adding circuit 37 with a distributor and driver 38 as an adapter part and display unit 39 connected on the output side. Thus, the summed, pre-programmed daily amount is digitally indicated in insulin units on the display unit 39. By means of key 40, the display can be reset to zero. Further, a pulse for a unit 41 for time display is tapped from the generator 35, which unit 41 consists of a driver 42 as an adapter part with a digital display 43 connected on its output side.

The daily profile of the dosing that is manually pre-programmed on the crosspoint distributor or is stored in the memory of the control installation, respectively, can upon need be recorded as an analog signal on an external logger, which is indicated with the reference 44. To that end, either a read-out path 46 which can be connected to the memory of the control device and consists in detail of a level converter 47 with a rate-current transducer 48 connected on its output side or a rate-current transducer 49 that is connected directly to the crosspoint distributor 30 is connected to the measuring unit of the logger 44 via an analog switch 45. Thereby, the time feed of the logger 44 is synchronously driven by the unit 50. A synchronization unit 51 serves the purpose of synchronizing of the program predetermined by means of the crosspoint distributor 30 and, if necessary, stored in the memory of the control device. Further, the programming device according to FIG. 2 exhibits actuation switches 52 and 53 which influence the generator 35 for the generation of the shift pulse or the unit 50 for controlling the logger, respectively, via the command memories 54 and 55. By means of switches 52 and 53, the logic circuit described can be controlled in such manner that entire daily profiles or individual time steps can be selectively read into or out of the memory of the control device II. Further, via switch 53, the quartz clock of the control device II is adjusted to the actual time of day. The switch 53 is designed as a touch contact, whereby, upon actuation, the display 41 and the quartz clock of the control devices II corresponding to the time grid of the crosspoint distributor 30 are keyed forward respectively by thirty minutes. Reference numeral 56 indicates a switch for switching on the current supply of the device for the above-described functions. To this end, the device also has a unit for current supply 57 allocated to it, which consists of an accumulator 58 with voltage monitor and display unit 59 as well as a unit for voltage stabilization 60.

In FIG. 3, the control device (corresponding to control installation II, FIG. 1) with pump drive control and monitoring integrated in the housing 68 comprises, in addition to the program plug 69 for coupling with plug 29, FIG. 2, the electrical or, respectively, electronic component parts 70 through 97: a program memory 70 is formed by a digital semiconductor memory 71, a so-called RAM, to which a logic circuit for addressing and reading-out of the values is allocated. An address counter 72 is pre-connected to the memory 71, which address counter is driven by the read-in path 31, 35 of the programming device according to FIG. 2 during reading-in of a program. During dosing control, the address counter 72 is simultaneously driven by a quartz clock 73 via a frequency divider 74. An intermediate memory 75 for a 4-bit byte is connected to the output side of the memory 71. Since time steps of 30 minutes can be pre-programmed on the programming device, the pending value is delivered in each case after 30 minutes by the actual program memory 71 to the intermediate memory 75. A monostable flip-flop 76 which is driven by the frequency divider 74 and transfers the pending value from memory 71 to the intermediate memory 75 by means of the switching signal serves the purpose of switching control. This measure has the advantage that the RAM 71 need not be continuously connected to the power supply 95. A BCD decoder 77 is connected on the output side of the intermediate memory, which BCD decoder transforms the control signal back into a decimal value. At the same time, the pulse output of a pulse generator 79 with a succeeding binary divider 80 is delivered to the pump drive control via a gate circuit 78.

Figure 4:
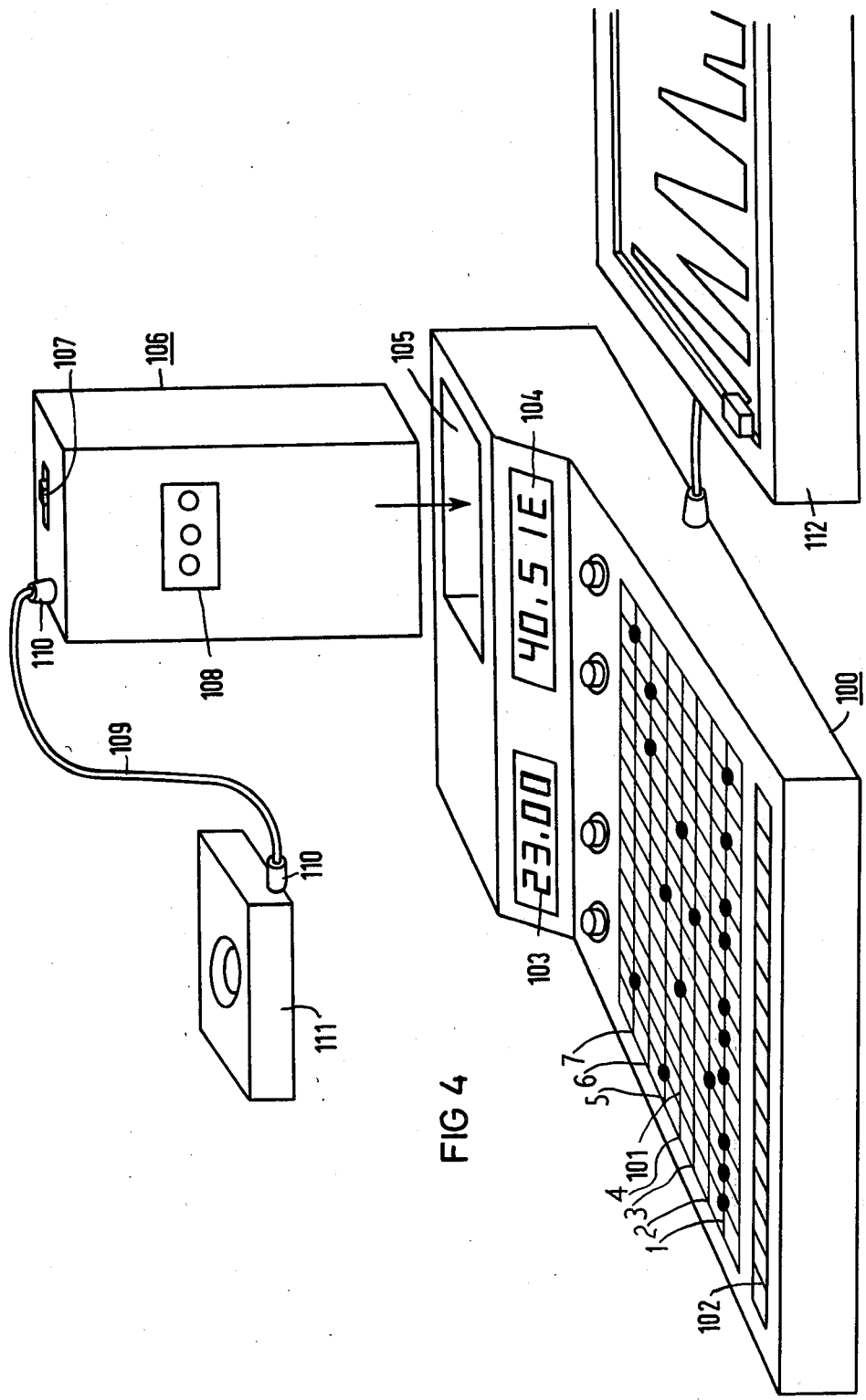
FIG. 4 is an exterior view in perspective of a device according to FIG. 1 with programming device, logger, as well as control device and microdosing unit, which, however, in deviation from FIG. 1, are connected by means of a line connection.

In the specific sample embodiment according to FIG. 4, the pump drive control 81 for the microdosing unit is integrated into the control device. The signal of the gate circuit 78 sets a monostable flip-flop 82 for the generation of a motor pulse. Via a driver stage 83, a step motor 84 is driven as the drive of a pump, which, for example, is a roller pump. Thereby, by means of the step motor 84, the pump drive for the roller pump is set in motion in detail, whereby the course of the pump rollers is monitored by means of the closing of a reed contact 85. By means of the alarm part 86, the function of the microdosing unit III can now be monitored. The monostable flip-flop 87, upon the running of the step motor 84, generates rectangular pulses that correspond to the motor frequency f, which rectangular pulses are displayed as pulses on a display unit 88. The rectangular pulses are simultaneously delivered to a further divider and counter stage 89 and counted. Since the number of the pulses generated by means of the reed contact 85 are correlated with the number of the step motor pulses in a correct running of the roller pump, the pump function can be audited by means of the comparison of the step motor pulses generated by the control device with the pulses of the reed contact 85. Under certain conditions, upon decoding in the recognition unit 90, a mechanical defect of the roller pump—in which the pump drive indeed receives step motor pulses but in which no roller movement ensues—is displayed at the display unit 91. The signal pulses generated by the reed contact 85 are further delivered to a divider and counter stage 92, which is always automatically set to zero at the beginning of the day by the frequency divider 74 of the quartz clock 73. The number of the reed pulses is a direct measure for the amount of liquid delivered; thus—given a corresponding calibration in insulin units—the number of insulin units actually delivered by the microdosing unit can be audited. Since, by means of the microdosing unit III, a predetermined total infusion amount for a patient in insulin units per day is not supposed to be exceeded, when such is the case, after decoding the signal by means of unit 93, an alarm is displayed on the display unit 94. In addition, the alarm part 86 exhibits a display unit 96 for the voltage stage of the battery 95 of the microdosing unit. An acoustic alarm emitter 97 for generating a beep is allocated to the display units 91, 94 and 96.

In FIG. 4, the external programming device is indicated with 100. It is designed about in the form of a typewriter, whereby a programming panel 101 with 48 columns and 7 rows occupies the operating plane. With such a programming panel 101, thus, 7 discrete infusion installments with a time grid of 30 minutes per column can be adjusted. Below the programming panel 101, there is a signal band 102 allocated to the 48 columns of the programming panel 101, upon which the physician can pre-program signals which signal the patient as an acoustical signal at a predetermined time of day for the ingestion of meals, etc. On the console-shaped part, digital display units 103, 104 for displaying the time of day and the total daily dosage as well as, if necessary, further control units and operating elements are arranged. The horizontal surface of the console part exhibits a receptacle 105 for the control installation in the device housing 106, into which, upon program read-in or, reading-out of the program, the control device 106 is manually inserted and electrically connected by means of the programming plug. After insertion of the control device 106, an automatic time synchronization between the control device 106 and the programming device 100 ensues.

In further practical embodiment, the control device 106 exhibits an operating element 107 with which, via a potentiometer, a calibration of the relative amplitudes of the delivery rate pre-programmed by means of the programming device 100 can ensue in absolute insulin units (IE) per hour. With this operating element 107, the patient can himself change the level of the daily dosage in an emergency and adjust the pre-programmed delivery rate to an altered situation. Further, a display field 108 for optical alarm display in case of malfunction is arranged on the control device 106. The control device 106 is shown connected with the microdosing unit 111 via an electrical cable 109. The microdosing unit 111 and the control device 106 each have releasable cable connections 110, so that the control device 106 and the microdosing unit 111 are not connected during the program loading from program device 100. A logger 112 for the analog display of the control program manually inserted on the crosspoint distributor 101 of the programming device 100 or, respectively, for reading-out the program stored in the control device 106 is allocated to the programming device 100. An ordinary time recorder can be used as the logger 112.

In the sample embodiments described, the daily profile of the dosage is in each case manually programmed-in on the separate programming device by the physician and the program is read into the memory of the control device 106 by means of a brief connection of the control device 106 with the programming device 100. In further embodiments of the invention, the programming can now also ensue in such manner that, upon programming, the information at the programming device is brought directly onto a program carrier. Thus, for example, punched cards, punched tapes or magnetic cards can be coded, which cards or tapes can be read by an appropriate read unit in the control device 106 and thus be read into the internal memory of control device 106. Such program carriers are particularly well-suited for documentation and the establishment of a program library. Specifically in the case of punched tapes and punched cards, the coding can also be undertaken in such manner that the hole punching reproduces a "quasi-analog" representation of the daily profile. In so doing, such program carriers can already be optically classified by the user.

Since, in the meantime, programmable semiconductor memories are also known in chip form, a further variation of the inventive installation is possible in which the memory unit in the control device 106 is interchangeable. A memory chip then serves as the programming carrier in the programming device such as 100 as well as serving as the internal memory medium in the control installation such as 106. In such a case, a library is constructed out of individual memory chips, out of which-under given conditions even without a further reprogramming—a memory chip with a program suitable for the patient can be taken and inserted in the control device. Thus, a specific loading of the program into the internal memory of the control device 106 by means of reading with read-out units is no longer necessary. Such variations, too, are included in the scope of the invention.

In the device according to German Offenlegungsschrift No. 2,451,424, the daily sequence of the infusion is pre-programmable on the programming panel of a control unit. Corresponding to the pre-programmed signals, the infusion is regulated by the control device. Thereby, corresponding with U.S. Pat. No. 3,809,871, the control program can be transferred, for example, to punched tapes. Such devices, however, can only be used for so-called bedside devices. It is also disadvantageous that the patient cannot move freely in the case of such a programmable infusion.

The invention disposes of these disadvantages in that a control device for the microdosing unit that can be carried on the body of the patient exhibits separate memory means, into which control programs that can be transferred at an external programming device. The control device and programming device are connected solely for program transfer. Otherwise, the patient is independent in his freedom of movement from the programming device, on which other individual patient programs can be written by the physician.

It will be apparent that many modifications and variations may be effected without departing from the scope of the novel concepts and teachings of the present invention.

We claim as our invention:

1. In a system for the pre-programmable infusion of liquids into a patient's body, the system has a microdosing unit adapted to controllably infuse a liquid into the patient's body based on signals received from a patient carriable control unit, the control unit is contained in a housing which includes a memory for storing a dosage control program to control the infusion of liquid by the microdosing unit, an improvement comprising:
   a socket part of a two-part means for connection affixed to the housing of the control unit,
   data transmission means within the control unit adapted to receive a dosage control program from said socket part of said two-part means for connection and write said program into said memory;
programming means separate from the control unit, said programming means including:
   a housing,
   a plug part of said two-part means for connection affixed to said housing such that a region of said housing partly surrounds said plug part,
   self-containing manually setable means for establishing another dosage control program which extends over a twenty-four hour period, and
   means for transmitting said another established dosage control program to said plug part of said two-part means for connection and then to said socket on the control unit only when said socket and plug parts of said two-part means for connection are connected together.

* * * * *